(12) United States Patent
Waldner et al.

(10) Patent No.: US 6,245,574 B1
(45) Date of Patent: *Jun. 12, 2001

(54) SENSORS

(75) Inventors: Adrian Waldner, Allschwil; René Beerli, Muenchenstein, both of (CH); Steven Mark Barnard, Wellesley Hills, MA (US)

(73) Assignee: Novartis AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/108,003

(22) Filed: Jun. 30, 1998

(30) Foreign Application Priority Data

Jul. 3, 1997 (CH) .................................. 1621/97

(51) Int. Cl.$^7$ .................................. G01N 33/20
(52) U.S. Cl. .................. 436/79; 422/56; 422/61; 422/82.05; 422/82.06; 422/82.07; 422/82.08; 436/73; 436/74; 436/172
(58) Field of Search .................. 422/56, 61, 82.05, 422/82.06, 82.07, 82.08; 436/73, 74, 79, 172

(56) References Cited

U.S. PATENT DOCUMENTS

| | | |
|---|---|---|
| 4,367,072 | 1/1983 | Vögtle et al. ........................ 436/501 |
| 4,973,394 | 11/1990 | Ross et al. .......................... 204/403 |
| 5,132,095 * | 7/1992 | Koshiishi et al. ................. 422/82.07 |
| 5,154,890 * | 10/1992 | Mauze et al. ..................... 422/82.07 |
| 5,300,439 | 4/1994 | Charlton .................................. 436/74 |
| 5,576,216 * | 11/1996 | Patchornik ............................ 436/86 |
| 5,723,340 * | 3/1998 | Karpf ..................................... 436/79 |

FOREIGN PATENT DOCUMENTS

| | | |
|---|---|---|
| 2119840 * | 9/1994 | (CA) . |
| 0 125 555 | 11/1984 | (EP) . |
| 95/26501 | 10/1995 | (WO) . |
| 97/39337 | 10/1997 | (WO) . |

OTHER PUBLICATIONS

Wang, E. et al., "Optical sensors for sodium, potassium, and ammonium ions based on lipophilic fluorescein anionic dye and neutral carriers", Analytica Chimica Acta, vol. 357, No. 1–2, 1997, pp. 85–90.
G.W. Pohl. et al. *Biophys. Struct. Mech.* 1976, 2, 119–137.*
B.F. Gisin et al. *Int. J. Pept. Protein Res.* 1979, 14, 356–363.*
E. Frehland et al. *Biophys. Chem.* 1982, 15, 73–86.*
O. S. Wolfbeis et al. *Anal. Chim. Acta* 1987, 198, 1–12.*
Y. Kawabata et al. *Anal. Chem.* 1990, 62, 1528–1531.*
Y.Kawabata et al. *Anal. Sci.* 1991, 7, 1465–1468.*
T. Werner et al. *J. Fluoresc.* 1992, 2, 93–98.*
J. Luo et al. in "Proc. East Asia Conf. Chem. Sens.," 2nd 1995, International Academic Publishers: Beijing, China, pp. 318–320.*

* cited by examiner

*Primary Examiner*—Arlen Soderquist
(74) *Attorney, Agent, or Firm*—Wenderoth, Lind & Ponack, L.L.P.

(57) ABSTRACT

Sensors for the qualitative and quantitative determination of $K^+$ ions in aqueous systems are described, which consist essentially of a carrier and an active layer applied to this carrier, whereby the active layer contains a polymer in which is dispersed at least one modified valinomycin, in which a radical of a fluorescence dye which emits in long waves, preferably an acridine or fluorescein, with an emission wave length of >550, is covalently bound.

22 Claims, No Drawings

SENSORS

The present invention relates to sensors with valinomycin derivatives for the optical determination by fluorescence of $K^+$ ions in aqueous systems, whereby the valinomycin derivatives contain a fluorescence dye which emits in long waves and is covalently bound by a bridging group; coating masses with these valinomycin derivatives; these valinomycin derivatives; an optical process for the qualitative and quantitative determination by fluorescence of $K^+$ ions in aqueous systems, and the use of the sensors for the optical determination by fluorescence of $K^+$ ions in aqueous systems.

The use of valinomycin as a highly specific ionophore for the determination of $K^+$ ions in aqueous systems, e.g. in blood, has been known for a long time. Natural valinomycin is a cyclodepsipeptide, which is made up of the elements D-valine (D-Val), L-lactic acid (L-Lac), L-valine (L-Val) and D-α-hydroxyisovalerianic acid (D-Hyisval), whereby said elements in the sequence indicated form a part sequence which is repeated three times in the 36-membered macro ring of valinomycin. The structure of natural valinomycin may also be described in abbreviated written form by the formula cyclo-(D-Val-L-Lac-L-Val-D-Hyisval)$_3$.

The macro ring of valinomycin forms a hollow cylinder in which $K^+$ ions are embedded. As a result of the change in charge thus induced, a discernible change is brought about in an indicator molecule, for example a fluorescence dye, which is present simultaneously, and this change can be referred to for the qualitative and quantitative determination of $K^+$ ions.

Conventional systems, which contain valinomycin as an ionophore, are multi-component systems which consist essentially of a polymer membrane which contains valinomycin as an ionophore, a fluorescence dye as an indicator molecule, and a lipophilic salt. The disadvantages of these systems is their poor stability and too long response time. Here, the poor stability is caused in the first instance by washing out of the active components, and the long response time is caused by the comparatively large physical distance between the ionophore and the fluorescence dye.

It has been found that the high specficity of valinomycin is maintained if a fluorescence dye as the indicator molecule is covalently bound by a bridging group to the macro ring of the valinomycin. It was also found that stable sensor systems with rapid response time are obtained if those valinomycins that are modified by covalent binding with a fluorescence dye are dispersed in a polymer membrane which is found, in such a case, as a layer on an appropriate carrier.

An object of the present invention is sensors for the qualitative and quantitative determination of $K^+$ ions in aqueous systems, which consist essentially of a carrier and an active layer applied to this carrier. The sensors according to the invention are characterised in that the active layer contains a polymer in which at least one modified valinomycin of formula I is dispersed,

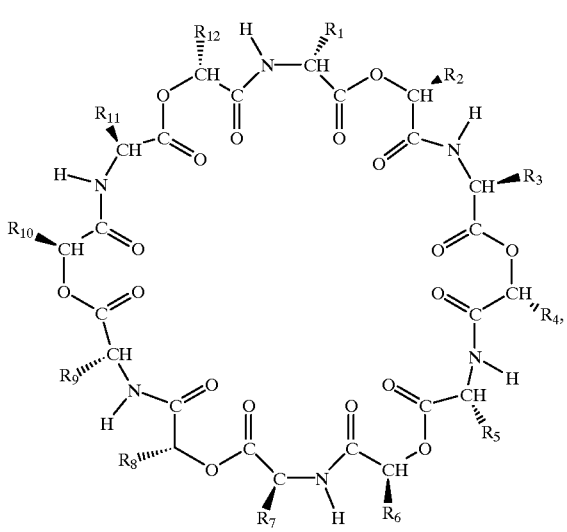

(I)

in which one of radicals $R_1$ to $R_{12}$ signifies a group of formula a,

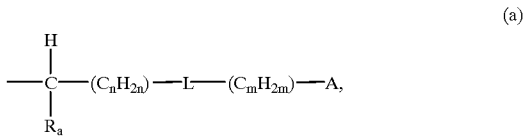

(a)

in which $R_a$ signifies hydrogen or methyl, m and n, independently of one another, denote 0 to 6, whereby in the alkylene group —$(C_nH_{2n})$— for n>0, a methylene group can be replaced by a phenylene or cycloalkylene radical, L is a bridging member formed by the reaction of two functional groups which are capable of reacting together, and A signifies the radical of a fluorescence dye emitting in long waves with an emission wave length of >550 nm, and the remaining radicals $R_1$ to $R_{12}$, independently of one another, signify methyl or isopropyl.

The compounds of formula I, in which the ionophore is covalently bound to a fluorescence dye by a bridging member are called fluoroionophores.

The carrier materials employed for the sensors according to the invention are opaque, translucent or preferably transparent materials. Suitable carrier materials are synthetic materials such as polycarbonates or acrylic glass, or mineral materials, metal oxides or mineral glass. Preferred carrier materials are organic or mineral glass. The carrier may be of any shape. Preferred shapes are for example sheets, cylinders, tubes, channels, ribbons or fibres.

Suitable polymers into which the fluoroionophores of formula I may be incorporated are those which enable a transparent or slightly opaque coating to be produced on the carrier. The polymers that may be considered are in particular acrylic polymers, such as poly-N,N-dimethyl acrylamide, polyethyl acrylate, polyethyl methacrylate, polyethylhexyl acrylate and acrylic polymers. Further suitable polymers are polyvinyl chloride, polyvinyl acetate, polyethylene, polypropylene and polyester, such as polyethylene terephthalate and polystyrene.

The thickness of the layer to be applied to the carrier may be from 0.01 to 100 μm, preferably 0.1 to 50 μm, especially 0.1 to 30 μm, most preferably 0.1 to 10 μm. The layer which is applied to the carrier may be transparent or slightly opaque. The layer is preferably transparent. Hydrophilic layers are also preferred.

Preparation of such layers may take place in a manner known per se, for example by dissolving a compound of formula I and a suitable polymer in a solvent, then applying the solution to the carrier and removing the solvent. The solution may be applied by pouring, or by employing processes which are known from lacquering technology. Such processes which may be named are in particular brushing, spin coating, spraying and screening processes. The layers are preferably applied by the spin coating process.

The solvents which may be considered are water, alcohols, ethers, esters, acid amides, halogenated hydrocarbons and ketones. Examples of such solvents are methanol, ethanol, n-propanol, isopropanol, diethyl ether, methyl isobutyl ether, tetrahydrofuran, dioxane, ethyl acetate, butyl acetate, dimethylformamide, dimethyl acetamide, methylene chloride, chloroform, acetone, methyl ethyl ketone and methyl isobutyl ketone. It is preferable to use readily volatile solvents, especially tetrahydrofuran, methylene chloride and acetone. One especially preferred solvent is tetrahydrofuran. The above-mentioned solvents may be used alone or as solvent mixtures. A viscosity of the coating compositions according to the invention which is appropriate for coating may be set by using an appropriate amount of the solvent respectively used.

A further object of the present invention is coating agents which contain a suitable polymer and a compound of formula I. According to one embodiment, these coating compositions may exist in the form of a powder which contains an appropriate polymer, a compound of formula I and optionally further additives in finely dispersed form. Suitable additives are for example lipophilic salts and softeners. According to another embodiment, the coating agents may exist in the form of solutions, such as those obtained by dissolving the above-mentioned powder mixtures in one of the above-mentioned solvents.

The groups L, which are formed by reacting two groups that can be reacted with one another, may be the following: —O—CO—; —CO—O—; —S—CO—; —CO—S—; —$NR_{13}$—CO—; —CO—$NR_{13}$; —$NR_{13}$—$SO_2$—; —$SO_2$—$NR_{13}$—; —O—CO—$NR_{13}$—; —$NR_{13}$—CO—O—; —S—CO—$NR_{13}$—; —$NR_{13}$CO—S—; —N($R_{13}$)—; —NH—CO—NH—, —NH—CS—NH— and —O—, whereby $R_{13}$ signifies H or $C_1$–$C_4$-alkyl. Preferred groups L are the ester groups, the carbonamide groups, the sulphonamide groups and the urea group. An especially preferred group is the carbonamide groups.

The suitable fluorescence dyes in question, which emit in long waves, are generally polycondensated aromatics from the group of acridines, benzopyrans and dibenzopyrans, which contain reactive groups that are suitable for binding with the modified valinomycins according to the invention. Such groups are for example —COOH, acid halides, such as —COHal and —$SO_2$Hal, whereby Hal signifies chlorine or bromine in particular, ester groups such as —CO—O-alkyl, —CO—O-aryl, —$SO_2$—O-alkyl and —$SO_2$—O-aryl, and groups of formula —($C_pH_{2p}$)—X, whereby X signifies OH, SH, halogen or $NH_2$ and p signifies 1 to 6. Such groups may be already present in the fluorescence dyes or may be added to them. Preferred fluorescence dyes which may be used according to the present invention are fluoresceins and rhodamines. Especially preferred fluorescence dyes are rhodamines, in particular rhodamines of the formula

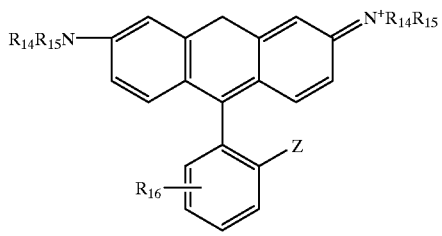

in which $R_{14}$ and $R_{15}$, independently of one another, denote $C_1$–$C_4$-alkyl and $R_{16}$ is preferably bonded in 4- or 5-position and signifies COOH, $SO_2$OH, $SO_2$Cl, $NH_2$, N=C=O, N=C=S, OH, $CH_2NH_2$, $CH_2$N=C=O, $CH_2$N=C=S, $CH_2$OH or $CH_2$Cl, and Z denotes —$COO^-$ or —$SO_3^-$.

Further preferred fluorescence dyes are rhodamines of formula

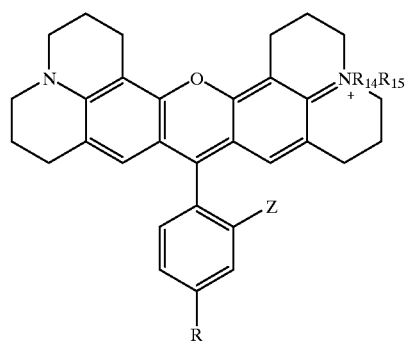

in which R signifies $SO_2$OH, $SO_2$Cl, N=C=O, N=C=S, COOH or $SO_2NHCH_2CH_2NH_2$, and Z denotes —$COO^-$ or —$SO_3^-$.

Also preferred are fluoresceins of formula

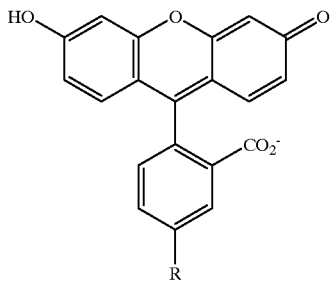

in which R signifies $NH_2$, N=C=O, N=C=S or COOH.

Preferred radicals A are those which are derived from fluorescence dyes, selected from the group comprising 4'-aminofluorescein, 5'-aminofluorescein, 3,6-diaminoacridine, 4'-amino-N,N,N',N'-tetraalkylrhodamine, 5'-amino-N,N,N',N'-tetraalkylrhodamine 4'-aminomethyl-N,N,N',N'-tetraalkylrhodamine, 5'-aminomethyl-N,N,N',N'-tetraalkylrhodamine, 4'-hydroxy-methyl-N,N,N',N'-tetraalkylrhodamine, 5'-hydroxymethyl-N,N,N',N'-tetraalkylrhodamine, sulphorhodamine, 4'-halogenmethylfluorescein and 4'-halogenmethyl-N,N,N',N'-tetraalkylrhodamine.

Natural valinomycin corresponds to a compound of formula I, in which $R_1$, $R_3$, $R_4$, $R_5$, $R_7$, $R_8$, $R_9$, $R_{11}$, and $R_{12}$ signify isopropyl, and $R_2$, $R_6$ and $R_{10}$ signify methyl. In the compounds of formula I according to the invention, one of radicals $R_1$ to $R_{12}$ denotes a group of formula a and the remainder of radicals $R_1$ to $R_{12}$ signify, independently of one another, methyl or isopropyl. According to the present invention, compounds of formula I are preferred, in which one of radicals $R_1$ to $R_{12}$ signifies a group of formula a and the remainder of radicals $R_1$ to $R_{12}$ have the same significance as in natural valinomycin. Especially preferred are compounds of formula I, in which one of radicals $R_1$ to $R_{12}$ signifies a group of formula a, in which $R_a$ is H, and the remainder of radicals $R_1$ to $R_{12}$ have the same significance as in natural valinomycin.

Further preferred compounds of formula I which may be contained in the sensors according to the invention are those in which one of radicals $R_3$, $R_7$ or $R_{11}$ signifies a group of formula a and the remainder of radicals $R_1$ to $R_{12}$ have the same significance as in natural valinomycin. Of these compounds of formula I, particular preference is in turn given to those in which n is 1, L signifies a group —CO—NH—, the group —($C_mH_{2m}$)— is a methylene or trimethylene group, and A signifies the radical of an aminoacridine or the radical of an amino- or aminomethylfluorescein.

For the greatest part, the compounds of formula I are new. The new compounds of formula I form a further object of the present invention. These new compounds correspond to formula I according to the above definition, with the proviso that where one of radicals $R_3$, $R_7$ or $R_{11}$ signifies a group —($C_nH_{2n}$)—L—($C_mH_{2m}$)—A and the remainder of radicals $R_1$ to $R_{12}$ have the same significance as in natural valinomycin, A does not signify the 5-dimethylamino-1-naphthyl radical if n is 3 and m is 0 and the alkylene group —($C_3H_6$)— is a trimethylene group —($CH_2$)$_3$— and the binding element L is —NH—$SO_2$—.

Especially preferred compounds of formula I are:
a) the compound of formula I, in which one of radicals $R_3$, $R_7$ or $R_{11}$ signifies a group —$CH_2$—CO—NH—$CH_2$—A, in which A is a fluorescein-4'-yl radical and the remainder of radicals $R_1$ to $R_{12}$ have the same significance as in natural valinomycin; and
b) the compound of formula I, in which one of radicals $R_3$, $R_7$ or $R_{11}$ signifies a group —$CH_2$—CO—NH—($CH_2$)$_3$—A, in which A is the 6-N-hexylaminoacridin-3-ylamino radical, and the remainder of radicals $R_1$ to $R_{12}$ have the same significance as in natural valinomycin.

In formula a, the group —($C_nH_{2n}$)— for n>0 signifies an alkylene group with 1 to 6 carbon atoms, which may be straight-chained or branched and in which a methylene group can be replaced by an aromatic or a saturated carbocyclic ring. Typical alkylene groups are methylene, 1,1-ethylene, 1,2-ethylene, 1,1-propylene, 1,2-propylene, 1,3-propylene, 1,1-butylene, 1,2-butylene, 1,3-butylene, 2,3-butylene, 1,4-butylene, 1,5-pentylene, 1,2-pentylene, 2,2-dimethyl-1,3-propylene and 1,6-hexylene. Groups —($C_nH_{2n}$)— in which n is 1, 2 or 3 are preferred. Saturated or aromatic rings, which may be contained in the alkylene group instead of a methylene group, are 1,4-cyclohexylene, 1,3-cyclopentylene, 1,4-phenylene, 1,3-phenylene and 1,5-naphthylene, whereby 1,4-cyclohexylene and 1,4-phenylene are preferred. 1,4-bis-methylenecyclohexane and 1,4-bis-methylenebenzene may be mentioned as examples of alkylene groups in which a methylene group can be replaced by a saturated or aromatic carbocyclic ring.

The group —($C_mH_{2m}$)— in formula a for n>1 signifies a straight-chained or branched alkylene group with 1 to 6, preferably 1 to 3 carbon atoms, and most preferably a methylene group. Typical alkylene groups are methylene, 1,1-ethylene, 1,2-ethylene, 1,1-propylene, 1,2-propylene, 1,3-propylene, 1,1-butylene, 1,2-butylene, 1,3-butylene, 2,3-butylene, 1,4-butylene, 1,5-pentylene, 1,2-pentylene, 2,2-dimethyl-1,3-propylene and 1,6-hexylene.

The compounds of formula I according to the invention may be produced whereby a compound of formula II,

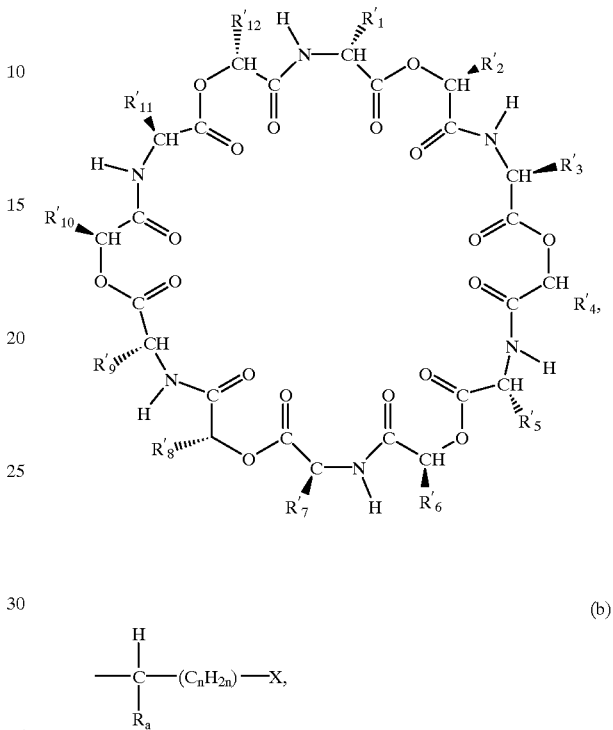

(II)

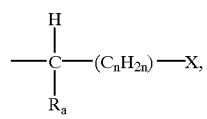

(b)

in which $R_a$ signifies hydrogen or methyl, n is a number from 0 to 6, whereby in an alkylene group —($C_2H_{2n}$)— for n>0 a methylene group can be replaced by a phenylene or a cycloalkylene radical, and X is a group selected from OH, SH, halogen, $SO_2$OH, $SO_2$Hal, $SO_2$O-alkyl, $SO_2$O-aryl, $NH_2$, NCO, NCS, CO—OH, CO-Hal, CO—O-alkyl, CO—O-aryl, and the remainder of radicals $R'_1$ to $R'_{12}$, independently of one another, signify methyl or isopropyl, is reacted with a compound of formula III $$Y—(C_mH_{2m})—A \quad (III)$$

in which Y is a group selected from COOH, CO-Hal, CO—O-alkyl, CO—O-aryl, $SO_2$—OH, $SO_2$-Hal, $SO_2$—O-alkyl, $SO_2$—O-aryl, OH, SH, Hal, $NH_2$, m is a number from 0 to 6, and signifies the radical of a fluorescence dye emitting in long waves with an emission wave length of >550 nm.

The reaction of a compound of formula II, in which one or radicals $R'_1$ to $R'_{12}$ signifies a group of formula b, with a compound of formula III is carried out in a manner known per se, whereby the respective reaction partners of formula II and of formula III are selected such that one reaction partner contains a group which is capable of reacting with the reactive group of the other reaction partner.

The valinomycin derivatives of formula I may be obtained in an advantageous manner, whereby
a) a compound of formula II, which contains a group of formula b, in which X signifies $COR_{16}$, whereby $R_{16}$ signifies Cl, phenoxy or benzotriazolyloxy, is reacted if desired in the presence of an acid-binding agent with a compound of formula III, in which Y signifies OH, SH or NHR$_{13}$, whereby R$_{13}$ is H or C$_1$–C$_4$-alkyl, to form compounds of formula I in which L represents a group —CO—O—, —CO—S—, —CO—N(R$_{13}$)—, b) a compound of formula II, which contains a group of formula b, in which X signifies OH, SH or NHR$_{13}$, whereby R$_{13}$ is H or C$_1$–C$_4$-alkyl, is reacted if desired in the presence of an acid-binding agent with a compound of formula III, in which Y signifies COR$_{16}$, whereby R$_{16}$ signifies Cl, phenoxy or benzotriazolyloxy, to form compounds of formula I in which L represents a group —O—CO—, —S—CO— or —NR$_{13}$—CO—;

c) a compound of formula II, which contains a group of formula b, in which X signifies SO$_2$R$_{16}$, whereby R$_{16}$ signifies Cl, phenoxy or benzotriazolyloxy, is reacted if desired in the presence of an acid-binding agent with a compound of formula III, in which Y signifies OH or NHR$_{13}$, whereby R$_{13}$ is H or C$_1$–C$_4$-alkyl, to form compounds of formula I in which L represents a group —SO$_2$—O— or —SO$_2$—N(R$_{13}$)—;

d) a compound of formula II, which contains a group of formula b, in which X signifies OH, SH or NHR$_{13}$, whereby R$_{13}$ is H or C$_1$–C$_4$-alkyl, is reacted if desired in the presence of an acid-binding agent with a compound of formula III, in which Y signifies SO$_2$R$_{16}$, whereby R$_{16}$ signifies Cl, phenoxy or benzotriazolyloxy, to form compounds of formula I in which L represents a group —O—SO$_2$— or —NR$_{13}$—SO$_2$—;

e) a compound of formula II, which contains a group of formula b, in which X signifies NCX$_1$, whereby X$_1$ is O or S, is reacted with a compound of formula III, in which Y signifies OH, SH or NHR$_{13}$, whereby R$_{13}$ is H or C$_1$–C$_4$-alkyl, to form compounds of formula I in which L represents a group —NH—CO—O—, —NH—CS—O—, —NH—CO—S—, NH—CS—S—, —NH—CO—N(R$_{13}$)— or —NH—CS—N(R$_{13}$)—;

f) a compound of formula II, which contains a group of formula b, in which X signifies OH, SH or NHR$_{13}$, whereby R$_{13}$ is H or C$_1$–C$_4$-alkyl, is reacted with a compound of formula III, in which Y signifies NCX$_1$, whereby X$_1$ is O or S, to form compounds of formula I in which L signifies a group O—CO—NH—, —O—CS—NH—, —S—CO—NH—, —S—CS—NH, N(R$_{13}$)—CO—NH or —N(R$_{13}$)—CS—NH;

g) a compound of formula II, which contains a group of formula b, in which X signifies OH or NHR$_{13}$, whereby R$_{13}$ is H or C$_1$–C$_4$-alkyl, is reacted in the presence of an acid-binding agent with a compound of formula III, in which Y signifies halogen, especially Cl, Br or I, to form compounds of formula I, in which L signifies a group —O— or —NR$_{13}$—, or h) a compound of formula II, which contains a group of formula b, in which X signifies halogen, especially Cl, Br or 1, is reacted in the presence of an acid-binding agent with a compound of formula III, in which Y signifies OH or NHR$_{13}$, whereby R$_{13}$ is H or C$_1$–C$_4$-alkyl, to form compounds of formula I, in which L signifies a group —O— or —NR$_{13}$—.

In the above-mentioned reactions, the acid-binding agents may be inorganic and organic bases. Suitable inorganic bases are in particular alkali- and alkaline earth metal hydroxides, especially NaOH and KOH, as well as alkali metal carbonates such as Na$_2$CO$_3$ and K$_2$CO$_3$. Suitable organic bases are in particular tertiary amines such as triethylamine, pyridine and dimethylaniline, as well as amidines and guanidines.

The starting materials for the production of the modified valinomycins of formula II are for the greatest part new compounds. The new compounds of formula I are similarly an object of the present invention.

The valinomycin derivatives of formula II which are required as starting materials according to the present invention may be produced by processes that are described in literature. The preparation of valinomycin derivatives of formula II, in which a D-valine element is replaced by D-lysine or D-glutamic acid, i.e. compounds of formula II, in which one of radicals R$_3$, R$_7$ or R$_{11}$ signifies —(CH$_2$)$_3$—NH$_2$ or —CH$_2$COOH, and the remainder of radicals R$_1$ to R$_{12}$ have the same significance as in natural valinomycin, is described for example in Khim. Prir. Soedin., volume 3, 1974, pages 346–358 (see English translation in "Chemistry of Natural Compounds" ©1975 Plenum Publishing Corporation, 227 West 17$^{th}$ Street, New York, N.Y, 1001, pages 350–358), also in Biophys. Struct. Mech. 2, pages 119–137 (1976), and also in Tetrahedron, Vol. 52, No. 4,1361–1378 (1996), or in Tetrahedron, Vol. 52, No. 4, 1379–1388 (1996). The remaining valinomycin derivatives of formula II may be produced in analogous manner from D- or L-α-amino acids and L-x-hydroxy acids of formulae

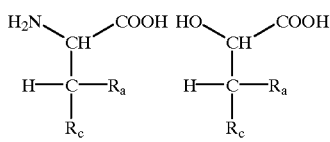

whereby in 11 of the 12 acids required in total, R$_a$ and R$_c$ both simultaneously signify hydrogen or both simultaneously signify methyl, and in the twelfth acid, R$_a$ is hydrogen or methyl and R$_c$ signifies a group —(C$_n$H$_{2n}$)—X as in the above definition.

Suitable α-amino acids are those which, apart from the α-amino group, also contain a further functional group, for example an amino group, a hydroxy group, a mercapto group or a carboxyl group. The functional groups which may be derived from these groups can also be considered, for example the isocyano and isothiocyano groups which may be derived from the amino group, and the acid halides, especially acid chlorides, which may be derived from carboxyl groups. It is preferable to use naturally occurring α-amino acids. Individual representatives of such naturally occurring α-amino acids which may be mentioned are serine, homoserine, threonine, cysteine, hydroxyproline, tyrosine, arginine, lysine, aspartic acid, glutamic acid, asparagine and glutamine. Particularly preferred α-amino acids are lysine, glutamic acid and aspartic acid.

Suitable α-hydroxy acids are those which, apart from the α-hydroxy group, also contain a further functional group, for example an amino group, a hydroxy group, a mercapto group or a carboxyl group. Individual representatives which may be mentioned are in particular α,β-dihydroxypropionic acid (glyceric acid), α-hydroxy-β-aminopropionic acid, α-hydroxy-ε-aminocaproic acid and malic acid.

The protecting groups required to produce the modified valinomycin derivatives of formula II according to the invention are known per se and may be taken for example from the above-mentioned references to literature.

The optical range in which the material may be excited as a sensor extends from the ultraviolet range to the almost infrared range. The fluorophore-ionophores to be used according to the invention have very appropriate absorption and emission wavelengths, which enable known inexpensive light sources requiring little power to be used, for example halogen or xenon lamps or light-emitting illuminating diodes. Preference is given to illuminating diodes as a source of excitation with a wavelength of about 400 nm and higher. Photodiodes may be used for example as detectors for fluorescence. Commercially obtainable optical fibres may be employed for excitation and detection. The sensor may therefore be replaced after usage on a patient.

The optical sensor is especially suitable for the quantitative determination of $K^+$ ions, which are present in blood plasma, in an aqueous environment, preferably by fluorescence spectrometry, whereby measuring conveniently takes place in the range of the emission maxima. Evaluations may be made in a short time with a high degree of accuracy, even with small concentrations (e.g. in the molar range to nanomolar range).

It is a quite particular advantage of the fluoroionophores according to the invention that measurements made with them are essentially independent of the pH value. There is therefore a much freer choice of fluoroionophores, since no proton exchange need take place on the fluorophore in order to detect the ions. In addition, it is possible to effect direct measurement of the analyte solution, which has considerable advantages. If desired, however, in certain cases measurements may be carried out in buffered analyte solutions, if for example fluorophores are used, which lead to a signal change through proton exchange.

The analyses may be undertaken for example directly in the body liquids (blood, urine, serum), natural waters or waste waters, whereby any harmful cations that are possibly present can be previously specifically bonded or removed. The composition according to the invention is especially suitable for determining physiological amounts of $K^+$ ions in aqueous media. These may be present for example in amounts ranging from 0.5 to 20 mmols.

Apart from the preferred fluorescence spectroscopy, other optical measurement methods may also be used, for example surface plasmon resonance spectroscopy, absorption spectroscopy, reflection spectroscopy, interferometry or surface-intensified Raman or fluorescence spectroscopy.

The invention also relates to a process for the optical determination of $K^+$ ions in aqueous measurement samples, in which a sensor according to the invention is brought into contact with said aqueous measurement sample and then measures the change in fluorescence of the fluorophore in the polymer layer.

The process according to the invention can be carried out for example in such a way that the carrier with the active polymer layer is secured in an optical cell, in which the active layer comes into contact with the measurement sample. The optical cell contains a window, through which the active layer can be excited by illumination and the emitted fluorescence rays can be measured by a spectrofluorometer. The wavelengths can be set at the absorption maximum for illumination and the emission maximum for measuring fluorescence. Intensity is measured as a function of time. The measurement system may be designed so that measurements are made discontinuously or continuously, whereby for example the measuring solution is pumped through the measuring cell. To determine unknown concentrations of cations, the system can be firstly gauged with measurement samples of known concentration, whereby the concentration is plotted as a function of the intensity of fluorescence.

If pH-dependent fluoroionophores are used, pH buffers are conveniently added to the measurement sample, since the sensitivity of measurement is dependent on the pH of the measuring solution owing to the pH dependence of the absorption spectrum and consequently also of the intensity of fluorescence of the fluorophore. In another embodiment, this pH dependence can also be specifically and mathematically taken into account. For example, the pH range of the measurement sample may be 4 to 8, more preferably 6.8 to 7.6. Appropriate buffers are for example citrate buffers and phosphate buffers. Further buffer systems are described in U.S. Pat. No. 4,645,744, in particular also those which are directly incorporated into the active layer so as to avoid making an addition to the measurement sample.

The invention further relates to the use of the optical sensor for the fluorescence-spectroscopic determination of $K^+$ ions.

The invention is explained more fully by the following examples.

A) Production of Preliminary Stages and Intermediates

A1: Production of N-tert.-butyloxycarbonyl-glutamic acid-1-benzyl-5-(2.2,2-trichloroethyl)ester

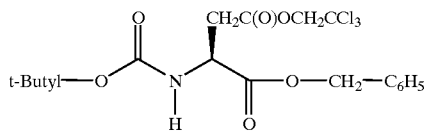

A solution of 25.00 g of N-tert.-butyloxycarbonyl-glutamic acid-1-benzylester and 8.0 ml of 2,2,2-trichloroethanol in 500 ml of dichloromethane is mixed with 16.82 g of dicyclohexyl carbodiimide and 0.91 g of dimethylaminopyridine. After stirring for 40 hours at room temperature, the dicyclohexylurea thus formed is filtered off and the filtrate is washed with 10% aqueous citric acid and then with saturated bicarbonate solution. The organic phase is dried over $MgSO_4$, concentrated totally and chromatographed on silica gel (eluant: hexane/ether 1:1). Yield: 32.22 g (93%). Melting point: 66°–67°. $[\alpha]_D$ ($CHCl_3$): –4.3°.

A2: Production of N-tert.-butyloxycarbonyl-glutamic acid-5-(2,2,2-trichloroethyl)ester

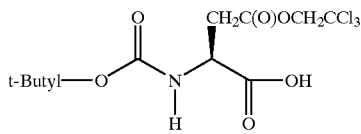

A solution of 31.28 g of N-tert.-butyloxycarbonyl-glutamic acid-1-benzyl-5-(2,2,2-trichloroethyl)ester in 500 ml of ethanol is hydrogenated at normal pressure and at room temperature in the presence of 1.17 g of palladium on activated carbon. The catalyst is separated by filtration and the filtrate is concentrated totally. Recrystallisation from ether/petroleum ether produces 15.29 g (yield: 61%) of the title compound. $^1H$ NMR: 7.6 (br, 1H) 5.3 (br, 1H); 4.8 (s, 2H); 4.4 (br, 1H), 2.6 (m, 2H); 2.3 (m, 1H); 2.1 (m, 1H); 1.4 (s, 9H).

A3: Production of the Intermediate of Formula

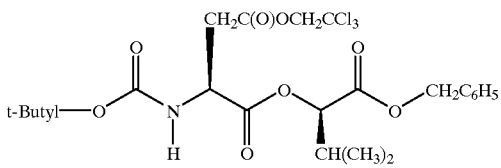

5.565 g of carbonyl diimidazole are added to a solution of 12.00 g of N-tert.-butyloxy-carbonyl-glutamic acid-5-(2,2,2-trichloroethyl)ester in 130 ml of dichloromethane. After stirring for 4 hours at room temperature, the addition of 5.498 g of D-hydroxyisovalerianic acid benzylester follows [1]. After a further 23 hours, washing takes place with 10% citric acid and saturated bicarbonate solution, whereby the aqueous phases are respectively extracted with dichloromethane. The organic phases are dried over $Na_2SO_4$ and concentrated totally. Chromatography on silica gel (eluant: hexane/ethyl acetate 3:1) and recrystallisation (ether/petroleum ether) of the mixed fractions produces 12.61 g (yield: 84%) of the diastereoisomeric pure title compound as white crystals having a melting point of 64.70–65.5°. $[\alpha]_D$ (C=1, $CHCl_3$): +9.4°; MS ($FAB^+$): 5.68 ([M+H]⁻).

A4: Cleavage of the tert.-butyloxycarbonyl Protecting Group of the Intermediate Produced According to A3:

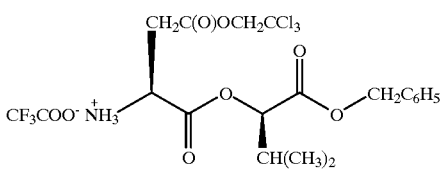

A solution of 11.01 g of compound A3 is mixed dropwise with 30 ml of trifluoroacetic acid. After 30 minutes at room temperature, the solvent is drawn off. In order to remove residues of trifluoroacetic acid completely, the oily residue is taken up in toluene and concentrated totally again, whereupon the ammonium trifluoroacetate of the above formula is obtained in a quantitative yield. $^1H$ NMR ($CDCl_3$) inter alia: 8.0 (br, 3H) ($NH_3$+); 7.3 (m, 5H) (benzyl protecting group); 4.78 (d) and 4.71 (d) (trichloroethyl protecting group).

A5: Production of the Intermediate of Formula

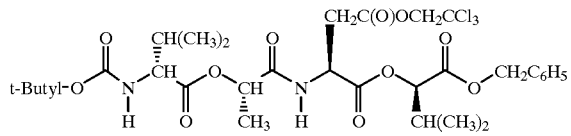

A solution of 1.241 g of (benzotriazol-1-yloxy)-tris-(dimethylamino)-phosphonium-hexafluorophosphate and 398 μl of N,N-diisopropylethylamine in 3 ml of dichloromethane is sprayed at 0° into a solution of 1.50 g of the above-described ammonium salt and 0.676 g of tert.-butyloxycarbonyl-D-valine-L-lactic acid [II] in 8 ml of dichloromethane. After 10 minutes, a further 557 μl of N,N-diisopropylethylamine is added, and after 30 minutes at 0°, heating is effected to room temperature and the mixture is stirred for 4 hours. The reaction mixture is diluted with dichloromethane and washed with 10% citric acid and saturated bicarbonate solution. The organic phase is dried over $Na_2SO_4$, concentrated totally and chromatographed on silica gel (eluant: hexane/acetic acid 3:1), whereupon 1.39 g (80% yield) of the title compound is obtained. $[\alpha]_D$ ($CHCl_3$, c=0.7): –9.6°; MS ($FAB^+$): 739 ([M+H]⁺).

A6: Cleavage of the tert.-butyloxycarbonyl Protecting Group of the Intermediate Produced According to A5 to Form the Ammonium Trifluoroacetate Salt

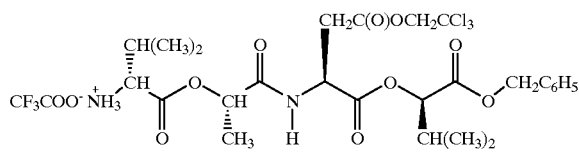

11.1 ml of trifluoroacetic acid are added dropwise to a solution of 3.978 g of the intermediate produced according to A5 in 4 ml of dichloromethane. After 1 hour, the solvent is drawn off, and the residue is taken up in toluene and concentrated totally again, whereupon the corresponding ammonium trifluoroacetate is obtained in quantitative yield. $^1H$ NMR ($CDCl_3$) shows inter alia: 5.3 (q, 1H); 5.2 (d, 1H); 5.1 (d, 1H); 4.75 (s, 2H); 4.1 (m, 1H); 1.6 (d, 3H); 1.1 (d, 6H); 0.95 (d, 6H); 0.9 (d, 6H).

A7: Production of the Intermediate of Formula:

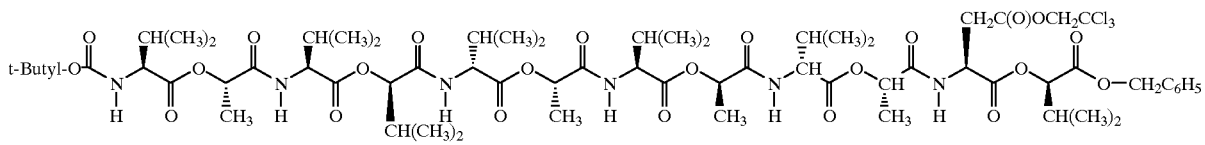

A solution of 4.467 g of the ammonium trifluoroacetate produced according to A6 and 4.513 g of N-tert.-butyloxycarbonyl-D-valine-L-lactic acid-L-valine-D-2-hydroxyisovalerianic acid-D-valine-L-lactic acid-L-valine-D-2-hydroxyisovalerianic acid [2] in 50 ml of dichloromethane is mixed with a solution of 3.033 g of (benzotriazol-1-yloxy)-tris(dimethylamino)phosphonium hexafluorophosphate and 2.68 ml of N,N-diisopropylethylamine in 15 ml of dichloromethane. After 3 hours at room temperature, the reaction mixture is diluted with dichloromethane and washed with 10% citric acid and subsequently with saturated bicarbonate solution. The organic phase is dried over $Na_2SO_4$, concentrated totally and chromatographed on silica gel (eluant: hexane/ethyl acetate A8: Cleavage of the benzyl- and the tert.-butyloxycarbonyl Protecting Group of the Intermediate Produced According to A7 to Form the Ammonium Trifluoroacetatecarboxylic Acid of Formula A solution of 500 mg of the trichloroethyl ester produced according to A9 in 10 ml of acetic acid and 600 mg of zinc powder is stirred vigorously for 22 hours at room temperature. The metallic zinc remaining behind is filtered off, and the concentrated filtrate is dissolved in 2 ml of dichloromethane, filtered, concentrated, dissolved in benzene and filtered again. The benzene solution is frozen with

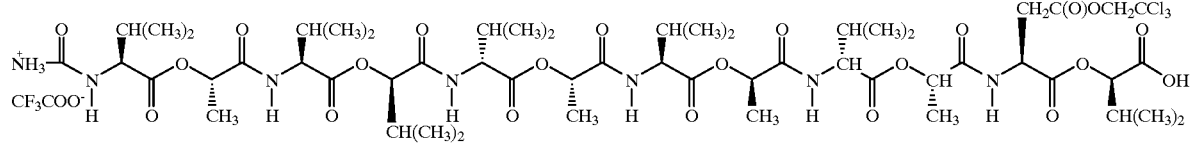

A solution of 10.45 g of the above-produced compound in 400 ml of methanol is hydrogenated at normal pressure and at room temperature in the presence of 560 mg of palladium on activated carbon (10%). After stirring vigorously for 40 minutes, the catalyst is removed by filtration and the filtrate is concentrated totally. The residue is dissolved in 20 ml of dichloromethane and mixed with 27 ml of trifluoroacetic acid. After 80 minutes, the solvent is evaporated and the residue is dissolved twice in toluene and again concentrated totally, whereupon the free acyclic compound is obtained in quantitative yield. $^1$H NMR (CDCl$_3$), signals of the amide protons: 8.35; 8.15; 8.0; 7.7; 7.55.

A9: Macrocyclisation to Form the Intermediate of Formula I, Wherein $R_1$, $R_3$ to $R_5$, $R_7$ to $R_9$ and $R_{12}$ are i-propyl, and $R_2$, $R_6$ and $R_{10}$ are Methyl, and $R_{11}$ Signifies Cl$_3$CCH$_2$O(O)CCH$_2$CH$_2$—

Over 20 minutes, a solution of 2.00 g of the acyclic compound produced according to A8 is stirred into 50 ml of thionyl chloride, before this is drawn off. To completely remove the last remains of thionyl chloride, the residue is taken up in 100 ml of benzene and totally concentrated by evaporation. The acid chloride thus obtained is dissolved in 300 ml of benzene and mixed with 0.60 ml of triethylamine. After 2 hours, the mixture is shaken with 100 ml of 10% citric acid, whereby the aqueous phase is subsequently extracted with ether twice more. The organic phases are dried over Na$_2$SO$_4$ and concentrated totally, whereupon 1.67 g (yield: 92%) of the macrocycle are obtained. $^1$H NMR (CDCl$_3$): 7.95 (d, J=7.4 Hz, 1H); 7.90 (d, J=7.4 Hz, 1H); 7.85 (m, 2H); 7.80 (d, J=7.2 Hz, 2H); 5.35 (q, J=7 Hz, 2H); 5.33 (q, J=7 Hz, 1H); 5.05 (d, J=3.1 Hz, 1H); 5.01 (d, J=3.2 Hz, 1H); 4.99 (d, J=3.4 Hz, 1H); 4.77 (s, 2H); 4.45 (dt, J=8.2, 6.6, 1H); 4.12 (dd, J=9.7 Hz, 8.0 Hz, 1H); 4.08 (m, 2H); 3.99 (dd, J=10.2 Hz, 6.2 Hz, 1H); 3.95 (dd, J=10.3 Hz, 5.9 Hz, 1H); 2.71 (ddd, J=17.0 Hz, 8.3 Hz, 6.4 Hz, 1H); 2.61 (ddd, J=17 Hz, 8 Hz, 7 Hz, 1H); 2.41–2.19 (m, 10H); 1.47 (d, J=6.8 Hz, 3H); 1.46 (d, J=7 Hz, 6H); 1.10 (d, J=6.5 Hz, 3H); 1.09 (d, J=6.5 Hz, 3H); 1.06 (d, J=6.6 Hz, 6H); 1.01–0.95 (m, 36H). $^{13}$C NMR (CDCl$_3$, multiplicities determined by the HETCOR experiment): 172.67 (s), 172.63 (s); 172.57 (s); 172.1 (5); 172.0 (s); 171.3 (5); 170.92 (s); 170.87 (s); 170.83 (s); 170.7 (5); 170.2 (s); 170.12 (s); 170.09 (5); 94.9 (s); 78.8 (d); 78.60 (d); 78.55 (d); 74.0 (t); 70.20 (d); 70.18 (d); 70.08 (d); 60.7 (d); 60.4 (d); 59.3 (d); 59.2 (d); 59.0 (d); 52.5 (d); 30.4; 30.23; 30.18; 30.11; 28.5; 28.40; 28.36; 28.33; 28.2; 24.6 (t); 19.8 (q); 19.7 (q); 19.5–19.2 (several unanalyzed signals, q)- 18.6 (q); 17.2 (q); 17.10 (q); 17.07 (q); 16.9 (q); 16.61 (q); 16.58 (q). MS (FAB$^+$): 1271 (M$^-$).

A10: Cleavage of the Trichloroethyl Protecting Group in Compound A9 to Form the Free Acid of the Macrocycle ($R_{11}$ is HO$_2$CCH$_2$C$_2$—)

liquid nitrogen in order to sublimate the benzene in a high vacuum, whereupon the free acid is obtained as a white powder in a 93% yield. $^1$H NMR (CDCl$_3$): 8.0–7.5 (6H); 5.4–5.25 (3H); 5.05 (2H); 4.95 (1H); 4.5–3.9 (6H); 2.55 (m, 1H); 2.4–2.1 (11H); 1.45 (m, 9H); 1.15–0.9 (48H).

B) Production of Valinomycin-fluoroionophores

Binding of a Fluorescein Derivative to the Fluoroionophore of Formula I, Wherein $R_1$, $R_3$ to $R_5$, $R_7$ to $R_9$ and $R_{12}$ are i-propyl, and $R_2$, $R_6$ and $R_{10}$ are Methyl, and $R_{11}$ is a Radical of the Following Formula

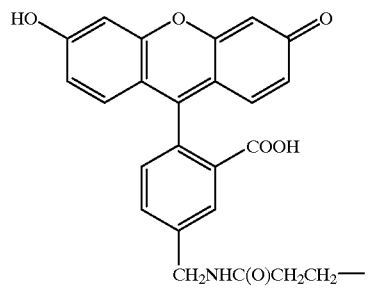

A solution of 19.4 mg of (benzotriazol-1-yloxy)-tris-(dimethylamino)-phosphonium hexafluorophosphate dissolved in 0.2 ml of dimethyl formamide and 11.9 μl of N,N-diisopropylethylamine is added to a solution of 7.0 mg of 5-aminomethylfluorescein (Molecular Probes Inc.) and 20 mg of the free acid of the macrocycle in 0.5 ml of dimethylformamide. After 21 hours at room temperature, the solution is diluted with dichloromethane and shaken against 10% citric acid. The organic phases are dried over Na$_2$SO$_4$, concentrated and chromatographed on silica gel (eluant: ethyl acetate/acetic acid 10:1). After gel filtration (Sephadex LH 20, eluant: isopropanol), 8.4 mg (32% yield) of the fluoroionophore are obtained. UV/VIS (methanol): 225 nm (ε=52,000); 276 nm (ε=10,000); 454 nm (ε=9500); 481 nm (ε=10,000). Fluorescence spectrum: excitation maximum: 498 nm; emission maximum: 522 nm; quantum yield ca. 1.0.

B2 Binding of an Acridine Dyestuff a) Production of N,N'-ditosyl-3,6-diaminoacridine 5.0 g of 3,6-diaminoacridine are suspended in a solution of 6.83 g of tosyl chloride in 150 ml of tetrahydrofuran (THF) and 3 ml of pyridine, and stirred for 22 hours at room temperature. The reaction mixture is concentrated and chromatographed under neutral conditions over Alox (eluant: tert.butylmethylether/methanol 4:1). Further chromatography over silica gel (eluant gradient: dichloromethane/methanol 20:1 to 8:1) produces at first 1.44 g (yield: 12%) of the title compound and then a further 2.15 g of the corresponding monotosyl compound. Spectroscopic data: MS (field desorption): 517 (M⁻). ¹H NMR (DMSO): 10.95 (br, 2H); 8.8 (s, 1H); 7.95 (d, 2H); 7.75 (d, 4H); 7.6 (s, 2H); 7.3 (m, 6H); 2.3 (5, 6H).

b) Production of N,N'-ditosyl-N-hexyl-3,6-diaminoacridine 4.50 g of N,N'-ditosyl-3,6-diaminoacridine, 3.59 g of 1-bromohexane and 1.46 g of powdered potassium hydroxide are dissolved in 100 ml of dimethylformamide, and stirred for 28 hours at room temperature. The reaction mixture is poured onto water and extracted three times with ethyl acetate. The organic phases are dried over $Na_2SO_4$, concentrated totally and chromatographed over silica gel (eluant gradient: toluene to toluene/ethyl acetate 4:1), whereupon 2.85 g of the title compound (yield: 55%) are obtained. ¹H NMR (CDCl₃): 8.65 (S, 1H); 7.95–7.1 (m, 1SH); 3.65 (t, 2H); 2.4 (s, 3H); 2.35 (s, 3H); 1.5–1.1 (m, 8H); 0.8 (t, 2H).

c) Production of N,N'-bistosyl-N-hexyl-N'-{3-[(tert.-butoxycarbonyl)amino]propyl}-3,6-diaminoacridine A solution of 3.22 g of N,N'-bistosyl-N-hexyl-3,6-diaminoacridine, 2.55 g of 3-[(tert.-butoxy-carbonyl)amino]-1-propylbromide [3] and 1.85 g of potassium carbonate in 50 ml of dimethylformamide is stirred for 25 hours at 70°, before the reaction mixture is poured onto water and extracted twice with ethyl acetate. The organic phases are dried over $Na_2SO_4$, concentrated by evaporation and chromatographed on silica gel (eluant: toluene/ethyl acetate 9:1), whereupon 2.98 g of the title compound (yield: 73%) are obtained as yellow crystals. Characteristic signals in the ¹H NMR spectrum (CDCl₃): 8.8 (s, 1H); 4.95 (m, 1H); 3.75 (t, 2H); 3.65 (t, 2H); 3.25 (q, 2H); 2.45 (s+5, 6H); 1.45 (5, 9H); 0.8 (t, 3H).

d) Production of N-(3-aminopropyl)-N'-hexyl-3,6-diaminoacridine

The compound produced according to c) is stirred into 30 ml of acetic acid/sulphuric acid (5:2) over the course of 26 hours at room temperature, before the reaction mixture is poured onto ice/2 M sodium hydroxide solution. This alkaline aqueous phase is extracted twice with ethyl acetate. The organic phases are washed with saturated sodium chloride solution, dried over $Na_2SO_4$, concentrated totally and chromatographed on silica gel (eluant gradient: dichloromethane to dichloromethane/methanol/triethylamine 16:4:1), whereupon 1.11 g of the title compound are obtained as orange crystals in 82% yield. Characteristic signals in the ¹H NMR spectrum (CDCl₃): 8.25(s,1H); 3.4 (t, 2H); 3.3 (t, 2H); 2.9 (t, 2H).

e) Binding of Valinomycin to Acridine Dyestuff to Form a Compound of Formula I, Wherein $R_1$, $R_3$ to $R_5$, $R_7$ to $R_9$ and $R_{12}$ are i-propyl, and $R_2$, $R_6$ and $R_{10}$ are Methyl, and $R_{11}$ is a Radical of the Following Formula

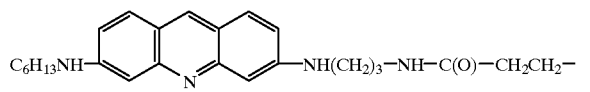

A solution of 8.0 mg of the dyestuff produced according to d) and 20.0 mg of the free acid of the valinomycin derivative produced according to A10 in 1 ml of dichloromethane is mixed with 5.9 mg of hydroxybenzotriazole, 100 μl of N,N-diisopropylethylamine and 16.6 mg of O-(1H-benzotriazol-1-yl)-N,N,N',N'-tetramethyluronium hexafluorophosphate. After stirring for 5 hours at room temperature, the mixture is diluted with dichloromethane and washed with water. The organic phases are dried over $Na_2SO_4$, concentrated totally and chromatographed on silica gel (eluant gradient: chloroform to chloroform/triethylamine 20:1), whereupon 19.7 mg of the fluoroionophore are obtained. MS FAB⁺: 1473 ([M+H]⁻); UV-VIS (methanol): 229 nm 15000); 264 nm (ε=58000); 290 nm (ε=25000); 470 nm (ε=60000), fluorescence spectrum: excitation maximum: 473 nm; emission maximum: 498 nm; quantum yield: 0,62.

Literature

[1] G. Losse, H. Klengel, *Tetrahedron* 1971, 27, 1423–1434.
[2] C. Zeggaf, J. Poncet, P. Jouin, M.-N. Dufour, B. Castro, Tetrahedron 1989, 45, 5039–5050.
[3] B. H. Lee, M. J. Miller, J. Org. Chem. 1983, 48, 24–31.

C) Production of a Sensor a) Production of a Polymer Stock Solution

A polymer stock solution is produced by dissolving 300 mg of a copolymer, produced from N,N-dimethylacrylamide and ethyl hexyl acrylate, in 3 ml of tetrahydrofuran.

b) Production of the Sensor Solution 1 mg of the fluoroionophore produced according to B2 e) and 1 ml of the polymer stock solution are placed in a 2 ml glass receptacle. The solution is stirred vigorously and used to produce sensors.

c) Application of the Sensitive Layer to the Carrier by the Spin Coating Process The carrier used was a purified round object carrier with a diameter of 18 mm. 200 μl of the sensor solution is applied to this carrier using a pipette, and it is then spun first of all for 15 seconds at 8000 rpm and then for 60 seconds at 10,000 rpm. Storage: the sensors were stored in Petri dishes with light excluded.

d) Test Apparatus

The test apparatus used was a conventional apparatus for fluorescence measurements. The beam of light is activated by means of a Wolfram halogen lamp. Prior to focussing on the sensor fitted in a through-flow cell, it focusses through several lenses and filters and is reflected through a dichroitic filter attached at an angle of 4500 to the activating beam of light. The emitted fluorescence light is trapped, passed through an emission filter and then focussed on a photodiode as a detector. Solutions with different concentrations of potassium ions (TRIS 0.1 M pH 7 buffer solution) are passed through the measuring cell. The intensity of the fluorescence light is recorded as voltage (mV) against the concentration of K⁺ ions (mM) and stored in a computer connected to the measuring apparatus. The results of the measurements are illustrated in the following.

| intensity of fluorescence (mV) | concentration of K + ions (mM) |
| --- | --- |
| 4 | 0.5 |
| 10 | 5 |
| 12 | 7 |
| 20 | 15 |
| 25 | 20 |
| 44 | 40 |

What is claimed is:

1. A sensor for the qualitative and quantitative determination of K⁺ ions in aqueous systems, which consist essentially of a carrier and an active layer applied to the carrier, wherein the active layer contains a polymer in which at least one modified valinomycin of formula I is dispersed, (I)

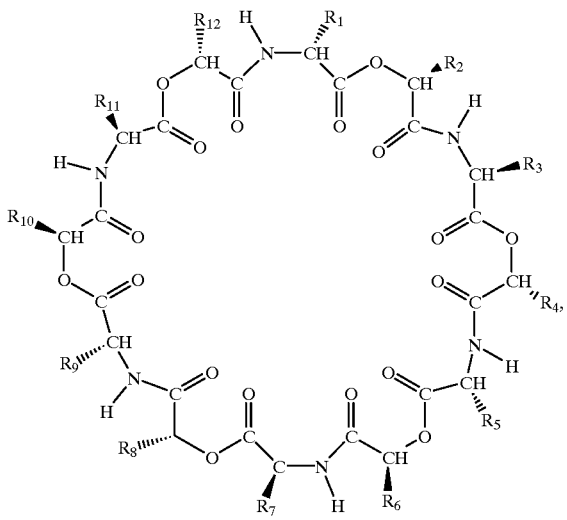

in which one of radicals $R_1$ to $R_{12}$ signifies a group of formula a, (a)

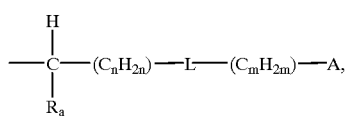

in which $R_a$ signifies hydrogen or methyl, m and n, independently of one another, denote 0 to 6, whereby in the alkylene group $-(C_nH_{2n})-$ for n>0, a methylene group can be replaced by a phenylene or cycloalkylene radical, L is a bridging member formed by the reaction of two functional groups which are capable of reacting together, and A signifies the radical of a fluorescence dye emitting in long waves with an emission wave length of >550 nm, or one of radicals $R_1$ to $R_{12}$ signifies a group of the formula:

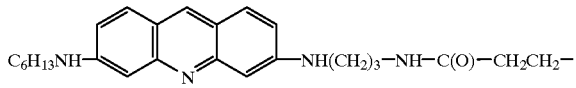

and the remaining radicals $R_1$ to $R_{12}$, independently of one another, signify methyl or isopropyl;
wherein an intensity of fluorescence of the sensor increases with increasing $K^+$ ion concentration.

2. The sensor according to claim 1, wherein the carrier is an organic or inorganic glass.

3. The sensor according to claim 1, wherein the polymer in which the compound of formula I is dispersed is selected from the group polyacrylic or—methacrylic acid esters or amides, polyvinyl chloride, polyvinyl acetate, polyethylene, polypropylene, polyterephthalic acid esters and polystyrene.

4. The sensor according to claim 1, wherein the thickness of the sensitive layer applied to the carrier is 0.01 to 100 μm.

5. The sensor according to claim 4, wherein the thickness of the sensitive layer applied to the carrier is 0.1 to 50 μm.

6. The sensor according to claim 4, wherein the thickness of the sensitive layer applied to the carrier is 0.1 to 10 μm.

7. The sensor according to claim 1, wherein the sensitive layer contains a compound of formula I, in which one of radicals $R_1$ to $R_{12}$ signifies a group of formula a, wherein $R_a$ is H, and the remainder of radicals $R_1$ to $R_{12}$ have the same significance as in natural valinomycin.

8. The sensor according to claim 1, wherein the sensitive layer contains a compound of formula I, in which n is 1, L signifies a group $-CO-NH-$, the group $-(C_mH_{2m})-$ is a methylene or trimethylene group and A signifies the radical of an aminoacridine or the radical of an amino- or aminomethylfluorescein.

9. Process for the optical determination by fluorescence of $K^+$ ions in aqueous measurement samples, wherein the measurement sample is brought into contact with a sensor system according to claim 1, and the change in fluorescence of the compound of formula I dispersed in the sensitive layer is measured.

10. The sensor according to claim 1, wherein A is a radical of a fluorescein compound or a radical of a rhodamine compound.

11. The sensor according to claim 10, wherein the radical of a fluorescein compound has the formula:

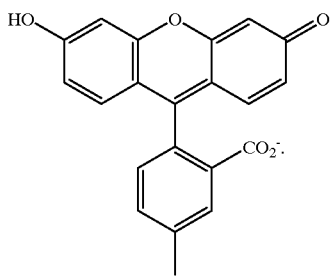

12. The sensor according to claim 10, wherein the radical of a rhodamine compound has the formula:

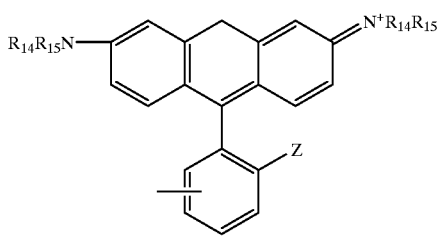

in which $R_{14}$ and $R_{15}$, independently of one another, denote $C_1$–$C_4$ alkyl and Z denotes $-COO^-$ or $-SO_3^-$, or the formula:

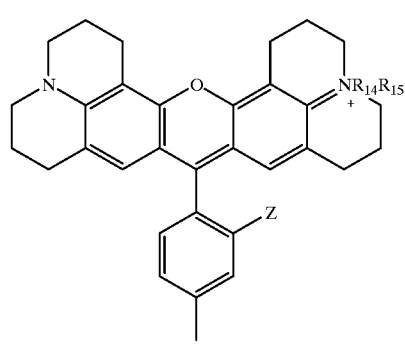

in which Z denotes $-COO^-$ or $-SO_3^-$.

13. The sensor according to claim 1, wherein one of the radicals $R_1$ to $R_{12}$ has the formula:

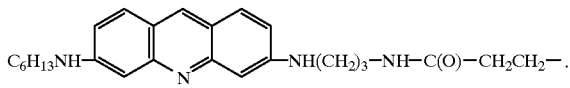

14. A coating composition comprising a polymer and a compound of formula I

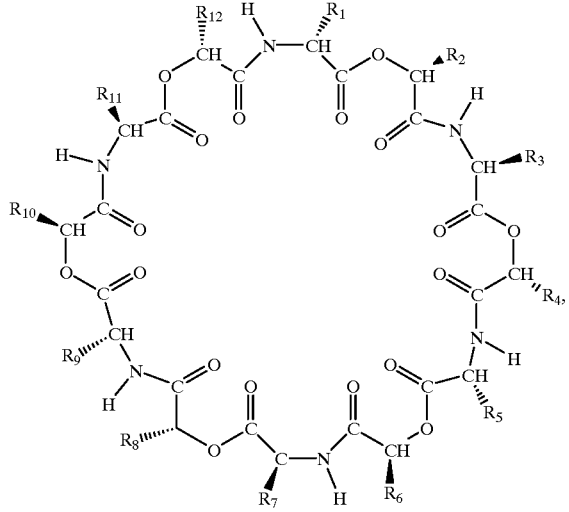
(I)

in which one of the radicals $R_1$ to $R_{12}$ is a group of formula a,

—CHR$_a$—(C$_n$H$_{2n}$)—L—(C$_m$H$_{2m}$)—A (a), wherein
  $R_a$ is hydrogen or methyl;
  each of m and n, independently of one another, is 0 to 6;
  in the alkylene group —(C$_n$H$_{2n}$)— for n>0, a methylene group can be replaced by a phenylene or cycloalkylene radical;
  L is a bridging member formed by the reaction of two functional groups which are capable of reacting together;
  A is a radical of a fluorescence dye emitting in long waves with an emission wave length of >550 nm;
  or one of the radicals $R_1$ to $R_{12}$ is a group of the formula:

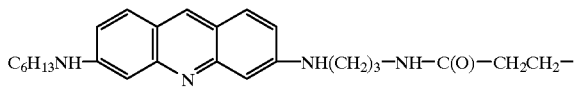

and each of the remaining radicals $R_1$ to $R_{12}$, independently of one another, is methyl or isopropyl;
wherein, in the presence of K$^+$ ions in aqueous systems, an intensity of fluorescence of the coating composition increases with increasing K$^+$ ion concentration.

15. The coating composition of claim 14, wherein the polymer is selected from the group consisting of polyacrylic or -methacrylic acid esters or amides, polyvinyl chloride, polyvinyl acetate, polyethylene, polypropylene, polyterephthalic acid esters and polystyrene.

16. The coating composition according to claim 14, wherein A is a radical of a fluorescein compound or a radical of a rhodamine compound.

17. The coating composition according to claim 16, wherein the radical of a fluorescein compound has the formula:

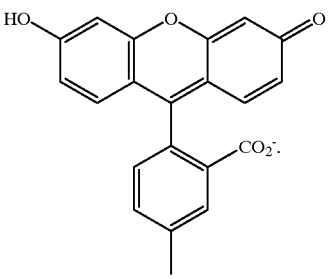

18. The coating composition according to claim 16, wherein the radical of a rhodamine compound has the formula:

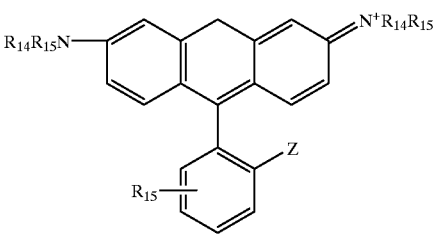

in which $R_{14}$ and $R_{15}$, independently of one another, denote $C_1$–$C_4$ alkyl and Z denotes —COO$^-$ or —SO$_3^-$, or the formula:

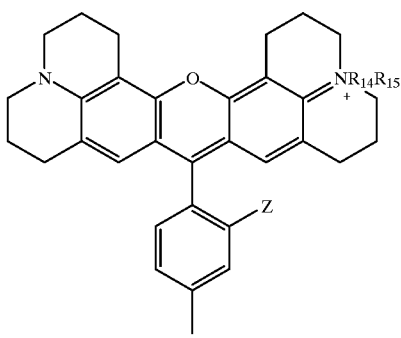

in which Z denotes —COO$^-$ or —SO$_3^-$.

19. The coating composition of claim 14, wherein one of the radicals $R_1$ to $R_{12}$ has the formula:

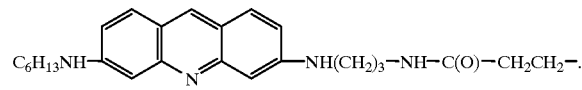

20. The coating composition of claim 14, in which one of radical $R_1$ to $R_{12}$ signifies a group of the formula a, wherein $R_a$ is H, and the remainder of the radicals $R_1$ to $R_{12}$ have the significance as in natural valinomycin.

21. The coating composition according to claim 14, wherein n is 1, L signifies a group —CO—NH—, the group —(C$_m$H$_{2m}$)— is a methylene or trimethylene group and A signifies the radical of an aminoacridine or the radical of an amino- or aminomethylfluorescein.

22. A compound of formula I

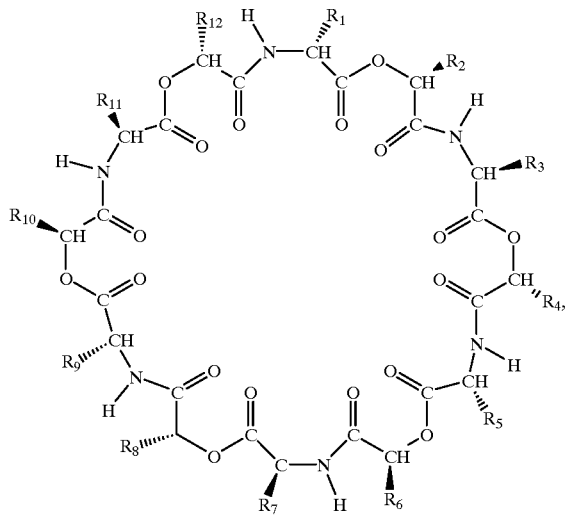

(I)

in which one of the radicals $R_1$ to $R_{12}$ is a group of formula a,

—CHR$_a$—(C$_n$H$_{2n}$)—L—(C$_m$H$_{2m}$)—A  (a), wherein $R_a$ is hydrogen or methyl;

each of m and n, independently of one another, is 0 to 6;

in the alkylene group —(C$_n$H$_{2n}$)— for n>0, a methylene group can be replaced by a phenylene or cycloalkylene radical;

L is a bridging member formed by the reaction of two functional groups which are capable of reacting together;

A is a radical of a fluorescence dye emitting in long waves with an emission wave length of >550 nm;

or one of the radicals $R_1$ to $R_{12}$ is a group of the formula:

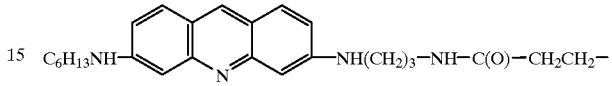

and each of the remaining radicals $R_1$ to $R_{12}$, independently of one another, is methyl or isopropyl, with the proviso that where one of the radicals $R_3$, $R_7$, or $R_{11}$ is a group —(C$_n$H$_{2n}$)—L—(C$_m$H$_{2m}$)—A and the remainder of radicals $R_1$ to $R_{12}$ are the same as in natural valinomycin, A is not the 5-dimethylamino-1-naphthyl radical if n is 3 and m is 0 and the alkylene group —(C$_3$H$_6$)— is a trimethylene group and the binding element L is —NH—SO$_2$—; wherein, in the presence of K$^+$ ions in aqueous systems, an intensity of fluorescence of the compound increases with increasing K$^+$ ion concentration.

* * * * *